US009435684B2

(12) United States Patent
Baldwin

(10) Patent No.: US 9,435,684 B2
(45) Date of Patent: Sep. 6, 2016

(54) INTEGRATED VIBRATION MEASUREMENT AND ANALYSIS SYSTEM

(71) Applicant: CSI Technology, Inc., Wilmington, DE (US)

(72) Inventor: Joseph C. Baldwin, Knoxville, TN (US)

(73) Assignee: Computational Systems, Inc., Knoxville, TN (US)

( * ) Notice: Subject to any disclaimer, the term of this patent is extended or adjusted under 35 U.S.C. 154(b) by 127 days.

(21) Appl. No.: 14/079,690

(22) Filed: Nov. 14, 2013

(65) Prior Publication Data
US 2014/0067289 A1    Mar. 6, 2014

Related U.S. Application Data

(63) Continuation-in-part of application No. 12/856,938, filed on Aug. 16, 2010.

(51) Int. Cl.
| | |
|---|---|
| *G01L 1/00* | (2006.01) |
| *G01L 3/00* | (2006.01) |
| *G06F 11/30* | (2006.01) |
| *G21C 17/00* | (2006.01) |
| *G01H 17/00* | (2006.01) |
| *G01H 1/00* | (2006.01) |

(52) U.S. Cl.
CPC .............. *G01H 17/00* (2013.01); *G01H 1/003* (2013.01)

(58) Field of Classification Search
CPC ......... G01H 1/003; G01H 1/00; G01M 7/00; G05B 23/02; G06F 11/00
USPC .................................................. 702/56, 185
See application file for complete search history.

(56) References Cited

U.S. PATENT DOCUMENTS

| | | | |
|---|---|---|---|
| 3,984,065 A | 10/1976 | Bosetti et al. | |
| 4,699,006 A | 10/1987 | Boxenhorn | |
| 4,984,464 A | 1/1991 | Thomas et al. | |
| 5,235,529 A | 8/1993 | Hanson et al. | |
| 5,398,538 A | 3/1995 | Williams et al. | |
| 5,412,985 A | 5/1995 | Garcia et al. | |
| 5,461,305 A * | 10/1995 | Kim ........................ | 324/76.11 |
| 5,633,811 A | 5/1997 | Canada | |
| 5,646,350 A | 7/1997 | Robinson | |
| 5,696,420 A | 12/1997 | Inanaga et al. | |
| 5,736,896 A | 4/1998 | Sakishita et al. | |
| 5,809,451 A | 9/1998 | Parsons et al. | |

(Continued)

FOREIGN PATENT DOCUMENTS

WO    8304326    12/1983

OTHER PUBLICATIONS

Mide, Volture Datasheet, Jun. 3, 2010, p. 1-24, http://www.mide.com/pdfs/Volture_Datasheet_001.pdf.

(Continued)

*Primary Examiner* — Michael Nghiem
(74) *Attorney, Agent, or Firm* — Luedeka Neely Group, P.C.

(57) ABSTRACT

A vibration data collection system performs an integration or differentiation process on incoming digitized vibration data in real time. The system uses a digital Infinite Impulse Response (IIR) filter running at the input data rate to provide the integration or differentiation function. With this approach, the system reduces hardware complexity and data storage requirements. Also, the system provides the ability to directly integrate or differentiate stored time waveforms without resorting to FFT processing methods.

5 Claims, 8 Drawing Sheets

(56) References Cited

U.S. PATENT DOCUMENTS

| | | |
|---|---|---|
| 5,854,994 A | 12/1998 | Canada |
| 5,895,857 A | 4/1999 | Robinson et al. |
| 5,965,819 A | 10/1999 | Piety |
| 6,070,681 A | 6/2000 | Catanzarite et al. |
| 6,138,078 A | 10/2000 | Canada |
| 6,505,131 B1 | 1/2003 | Henrot |
| 6,584,386 B2 | 6/2003 | Feser et al. |
| 6,845,135 B2 | 1/2005 | Du |
| 6,889,553 B2 | 5/2005 | Robinson et al. |
| 7,010,445 B2 | 3/2006 | Battenburg et al. |
| 7,024,172 B1 | 4/2006 | Murphy et al. |
| 7,164,853 B2 | 1/2007 | Tomita |
| 7,324,919 B2 | 1/2008 | Lindberg |
| 7,424,403 B2 | 9/2008 | Robinson et al. |
| 7,561,200 B2 | 7/2009 | Garvey |
| 2003/0034984 A1* | 2/2003 | Murata .................. 345/589 |
| 2006/0150738 A1 | 7/2006 | Leigh |
| 2009/0058696 A1* | 3/2009 | Baldwin .................. 341/110 |
| 2009/0125269 A1* | 5/2009 | Acuff .................. G01R 31/3177 |
| | | 702/107 |
| 2009/0224158 A1 | 9/2009 | Haselman et al. |
| 2009/0228628 A1 | 9/2009 | Standfield |
| 2011/0257934 A1 | 10/2011 | Dimino et al. |
| 2012/0041695 A1* | 2/2012 | Baldwin .................. 702/56 |
| 2014/0324367 A1* | 10/2014 | Garvey, III .......... G01D 18/00 |
| | | 702/56 |

OTHER PUBLICATIONS

M. A. Al-Alaoui, Novel Digital Integrator and Differentiator, Electronics Letters 3, Feb. 18, 1993, pp. 376-378, vol. 29, No. 4.

Roger I Lemieux, Reduction of the Ski Slope Effect When Integrating from Acceleration to Velocity, 1994, 11 pages., Computational Systems, Inc.

Lance D. Slifka, An Accelerometer Based Approach to Measuring Displacement of a Vehicle Body, Apr. 2004, 66 pages, University of Michigan-Dearborn.

* cited by examiner

INTEGRATED VIBRATION MEASUREMENT AND ANALYSIS SYSTEM

RELATED APPLICATIONS

This application claims priority as a continuation-in-part of U.S. patent application Ser. No. 12/856,938 titled "Integrated Vibration Measurement and Analysis System" filed on Aug. 16, 2010, which is now abandoned.

FIELD

This invention relates to the field of machine vibration measurement for detecting mechanical, electrical, and electromagnetic fault conditions in an operating machine. More particularly, this invention relates to a system for performing real-time digital processing of time domain signals indicative of vibration produced by a machine.

BACKGROUND

Problems with Conventional Analog Integration in Machine Monitoring Systems

Conversion from one type of vibration-related signal (such as acceleration) to another vibration-related signal (such as velocity or displacement) is a common requirement for vibration monitoring systems. A typical example is the conversion from acceleration to velocity by integration of the acceleration signal. Similarly, the opposite conversion can be performed by differentiating a velocity signal. In the past, these conversions have been done using analog hardware filters. Such conversions have also been done after data collection, using software that performs a Fast Fourier Transform (FFT) and operates on the transformed data in the frequency domain.

An ideal hardware integrator is shown in FIG. 4. This circuit directly converts an acceleration (or velocity) signal to velocity (or displacement) with a conversion factor proportional to 1/R1×C2. Unfortunately, this circuit is not suitable in practice due to the high DC gain. The circuit quickly saturates due to offset currents and voltages of the operational amplifier. A more refined approach is shown in FIG. 5, where the addition of R2 and C1 limit the low-frequency response of the operational amplifier to prevent saturation. The appropriate selection of R1 and C2 gives a direct conversion between units, (e.g. 61.45/f for conversion of acceleration to velocity). This approach converts the signal directly, prior to data acquisition, so that no additional data processing is required. However, it offers no flexibility in changing the conversion factors and is subject to variability in hardware component values. Also, it consumes large amounts of circuit board real estate due to the physically large components required for low-frequency operation.

Another prior art approach to the conversion is to digitize the vibration signal using an analog-to-digital converter (ADC), transform to the frequency domain using FFT methods, and apply integration or differentiation on the frequency spectrum. This process is depicted in FIG. 6. Disadvantages of this approach include the lack of ability to do the conversion process continuously in real-time and the system complexity required to perform the FFT. Also, creation of an integrated time waveform requires extensive data processing (i.e., forward and inverse FFT computations). Finally, the FFT method assumes the signal is stationary which may not be true for dynamic signal conditions and could lead to errors in the re-creation of the time domain signal.

What is needed, therefore, is a conversion process that reduces hardware complexity, reduces data storage requirements, and provides for direct integration or differentiation of time-domain vibration waveforms without resorting to FFT methods.

Problems with Conventional Analog Signal Conditioning in Machine Monitoring Systems As shown in FIG. 7, a typical vibration analysis channel 50 consists of an analog front-end 52, an analog-to-digital converter (ADC) 54, and a digital signal processor (DSP) 56 or microcontroller. The analog front-end 52 usually contains a vibration sensor 58, an input amplifier 60, an AC coupling amplifier 62, analog integrator 64, a variable-gain amplifier 66, and a low-pass anti-aliasing filter and high-pass filter 68.

Such implementations of front-end signal conditioning functions in the analog domain cause numerous problems. Calibration is required due to component variations which cause the sensitivity and bandwidth of the signal path to vary. Analog components require relatively large amounts of space on the printed circuit board, and they consume large amounts of power for low-noise designs. They are also somewhat limited in terms of programmability. For systems designed for use in hazardous environments, reduced voltage and capacitor allowances force tradeoffs in noise and bandwidth in the analog signal path.

What is needed, therefore, is a machine vibration measurement system in which the front-end signal conditioning functions are performed in the digital domain, such as in a field programmable gate array (FPGA) or application-specific integrated circuit (ASIC), or as an algorithm in a digital signal processor.

A discussion of prior art machinery vibration analyzers will provide further context for understanding the various advantages of the machine vibration measurement system of the present invention. U.S. Pat. No. 5,412,985 to Garcia et. al. (hereinafter "Garcia), U.S. Pat. No. 5,633,811 to Canada et. al. (hereinafter "Canada"), U.S. Pat. No. 5,965,819 to Piety et. al. (hereinafter "Piety"), and US 2006015738A1 to Leigh (hereinafter "Leigh") are representative of such prior art machinery vibration analyzers.

Garcia et. al. discloses using either an IIR or FIR filter in a machinery vibration analyzer. It incorporates analog signal conditioning, including integration, and it requires anti-aliasing filtering before analog-to-digital conversion.

Canada describes a machinery vibration analyzer having analog signal conditioning, including analog integration, direct-current (DC) offset, gain control, and a fixed frequency low-pass anti-aliasing filter. In addition to this analog circuitry, the disclosure teaches about digital filtering, decimation, and sigma-delta noise shaping.

Piety describes parallel processing in a vibration analyzer wherein an analog sensor signal representing a measured property of an operating machine is split and simultaneously processed through at least two parallel circuits. Each of these circuits has input filters, integrators, DC offsets, amplifiers, and circuit filters prior to parallel analog-to-digital conversion. Each parallel circuit is capable of performing different types of signal analyses with varying analog signal conditioning and sampling rate requirements.

Leigh describes machinery vibration analysis that involves deriving multiple types of vibration signals from one vibration signal and selecting a digital acceleration signal or first digital integration to convert a digital acceleration signal to a velocity signal or a first digital integration to convert a digital acceleration signal to a velocity signal followed by a second digital integration to convert a velocity signal to a displacement signal in a machinery vibration analyzer. The vibration analyzer according to Leigh incorporates analog signal conditioning acting on the analog signal from an accelerometer, including scaling, DC offset, and anti-alias filtering. Leigh requires selection of a sampling frequency before digitizing the analog acceleration signal using an analog-to-digital converter (ADC).

The machinery vibration analyzers disclosed by Garcia, Canada, Piety, and Leigh do not teach about the following elements found in certain embodiments of the present invention:
  (a) fixed analog-to-digital sampling rate in an analog-to-digital converter;
  (b) flexible field programmability for a parallel vibration signal processing circuit;
  (c) parallel vibration signal processing in an FPGA;
  (d) a parallel vibration signal processing in an ASIC;
  (e) an ideal integrator transfer function using a difference equation;
  (f) a synthesized sampling rate using an arbitrary resampler;
  (g) a digital filter to remove a direct current (DC) component from a vibration signal;
  (h) switch control circuitry for switching between a non-rechargeable battery and an energy harvester power source;
  (i) a digital implementation of an anti-aliasing filter;
  (j) a digital implementation of a scaling circuit;
  (k) replacement of a traditional analog signal conditioning component calibration with a digital design that does not require analog calibration;
  (l) a single-step double integrator in the digital domain that converts an acceleration signal to a displacement signal; and
  (m) a field programmable switching device that is operable to direct any one of a plurality of digital vibration inputs to any one of a plurality of outputs.

U.S. Pat. No. 5,696,420 to Inanaga et. al. (hereinafter Inanaga) and U.S. Pat. No. 7,164,853 to Tomita (hereinafter Tomita) describe controlling devices for detecting a motion of the device itself.

Inanaga describes a control device for detecting a swinging motion of a person's head wearing audio headphones. The Inanaga device uses a vibration type gyroscope that reads a control signal and controls an audio signal to create virtual sound source positioning in reference to a direction of the listener wearing headphones. Inanaga teaches using a digital integrator and digital differentiator with a digital filter, such as an infinite impulse response (IIR) digital filter, finite impulse response (FIR) digital filter, or the like. The vibration type gyroscope of Inanaga is a control device and not a measurement apparatus like the present invention. For example the following features that are required for the Inanaga apparatus are not required for the present invention (that is, these features may be avoided individually or collectively with the present invention):
  (a) an amplitude-modulated detection signal is converted into a digital signal;
  (b) a modulated analog piezoelectric signal output is demodulated to obtain a correct detection output;
  (c) piezoelectric elements are integrated into the apparatus body;
  (d) a pair of piezoelectric elements are used for detection, and a pair of piezoelectric elements are used for driving, and a differential amplifier is used for obtaining a differential output between output signals of the pair of piezoelectric elements for detection; and
  (e) a control signal is supplied from the outside.

Tomita describes a vibration correcting optical control device. This device detects vibration caused by hand movement or the like to provide control for correction of optical blur. This disclosure mentions using a low pass filter such as an FIR filter or an IIR filter. The disclosure also teaches a digital integrating operation unit. The disclosure according to Tomita requires multiple things that are not required in the present invention (that is, these features may be avoided individually or collectively):
  (a) an angular speed sensor capable of detecting coriolis force;
  (b) a vibration detection and signal processing unit;
  (c) a reference value calculation unit;
  (d) determination of an abnormal vibration indication is required before performing an integration or a differentiation; and
  (e) a drive signal calculation unit.

Furthermore, a chasm of undisclosed applications exists between the Inanaga and Tomita control devices and the machinery vibration analyzer of the present invention. Even if the disclosures of Inanaga and Tomita are combined, the combination fails to describe or suggest several important features of various embodiments of the present invention, such as:
  (a) measuring a vibration signal that is indicative of the vibration level of a machine;
  (b) measuring a parameter of a machine that is indicative of a machine fault condition or machine performance;
  (c) sensing an acceleration parameter of a machine;
  (d) field programmability;
  (e) FPGA processing;
  (f) ASIC processing;
  (g) selections;
  (h) removing a DC signal component;
  (i) sampling an analog vibration signal at a fixed sampling rate; and
  (j) synthesizing other sampling rates from a fixed sampling rate.

Besides those listed here, there are many other examples of features desired for machinery vibration analysis that are not provided by Inanaga or Tomita.

SUMMARY

The above and other needs are met by a vibration data collection system that performs the integration or differentiation process on incoming digitized vibration data in real time. The system uses digital Infinite Impulse Response (IIR) filters running at the input data rate to provide the integration or differentiation function. With this approach, the system reduces hardware complexity and data storage requirements. Also, the system provides the ability to directly integrate or differentiate stored time waveforms without resorting to FFT processing methods.

In one preferred embodiment, the invention provides a real-time signal conversion apparatus for use in measuring vibration levels of a machine that are indicative of machine fault conditions. The signal conversion apparatus includes a sensor for measuring an analog signal that is indicative of a mechanical or electrical or electromagnetic fault condition of an operating machine. Some example fault conditions include mechanical imbalance, misalignment, bent shaft, soft foot, looseness, resonance, broken rotor bar, broken gear tooth, bearing defect, oil whirl, oil whip, phase imbalance, and turn-to-turn short circuit. Typically the sensor is a vibration sensor such as an accelerometer or velocity transducer or proximity probe, and occasionally the sensor is a motor flux coil or a current clamp. In addition to these dynamic signal measuring transducers, some embodiments use more static sensors, typically providing 0 to 5 V or 4 to 20 mA outputs, to measure an asset health characteristic such as a thickness, a temperature, a corrosion effect, or a material property. An analog-to-digital conversion (ADC) circuit samples the analog signal at an input data rate to convert the analog signal into a first digital signal. A digital infinite impulse response filter receives the first digital signal at the input data rate and performs a mathematical operation at the input data rate on the first digital signal to generate a second digital signal substantially in real time. The second digital signal is indicative of the condition of the machine, and the mathematical operation is selected from the group consisting of an integration operation and a differentiation operation.

In another aspect, the invention provides a method for measuring vibration characteristics of a machine that are indicative of fault conditions of a machine. In a preferred embodiment, the method includes:
 (a) sensing vibration of the machine and generating an analog vibration signal based on the sensed vibration;
 (b) sampling the analog vibration signal at a fixed sampling rate to generate a first digital vibration signal;
 (c) synthesizing other sampling rates based on the fixed sampling rate of the first digital vibration signal, thereby eliminating any need for an anti-aliasing filter;
 (d) high-pass filtering the first digital vibration signal to remove direct current (DC) components; and
 (e) performing a first mathematical operation on the first digital vibration signal to generate a second digital vibration signal that is indicative of the vibration characteristics of the machine, wherein the first mathematical operation is selected from the group consisting of an integration operation and a differentiation operation.

In preferred embodiments, no signal conditioning step, such as gain amplification, DC removal, anti-aliasing filtration, or high-pass filtration, is performed between the vibration sensing step (a) and the sampling step (b).

In yet another aspect, the invention provides a real-time signal conversion apparatus for use in measuring vibration characteristics of a machine that are indicative of machine fault conditions. The signal conversion apparatus of one embodiment includes a vibration sensor for sensing vibration of the machine and generating an analog vibration signal based on the sensed vibration, where the analog vibration signal is indicative of a fault condition of the machine. An analog-to-digital conversion (ADC) circuit samples the analog vibration signal to generate a first digital vibration signal. A digital high-pass filter filters the first digital vibration signal to remove direct current (DC) components. A digital infinite impulse response filter performs a mathematical operation on the first digital vibration signal to generate a second digital vibration signal that is indicative of the vibration level of the machine, where the mathematical operation is selected from the group consisting of an integration operation and a differentiation operation. In this embodiment, the analog vibration signal is provided to the analog-to-digital conversion circuit without gain amplification and without anti-aliasing filtration.

In alternative embodiments, instead of using a vibration sensor to collect machine vibration information and to produce an analog signal revealing mechanical fault conditions, a flux coil sensor or a current clamp sensor is used to measure machine electromagnetic information and to produce an analog signal revealing motor rotor and motor stator faults. Further, a current clamp type sensor or other sensor capable of measuring either electrical current or electrical voltage is used to measure machine current and/or voltage information, further revealing motor rotor and motor stator faults. Those skilled in the art recognize how analog signals from these alternative sensors are processed following the examples of vibration signal processing described herein.

In some embodiments, the digital high-pass filter and the digital infinite impulse response filter are implemented in a field programmable gate array (FPGA). The FPGA may include an embedded processor for controlling storage and processing of data associated the first digital vibration signal or the second digital vibration signal. In other embodiments, the digital high-pass filter and the digital infinite impulse response filter are implemented in an application specific integrated circuit (ASIC).

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Real-Time Digital Integrator

Figure 1:
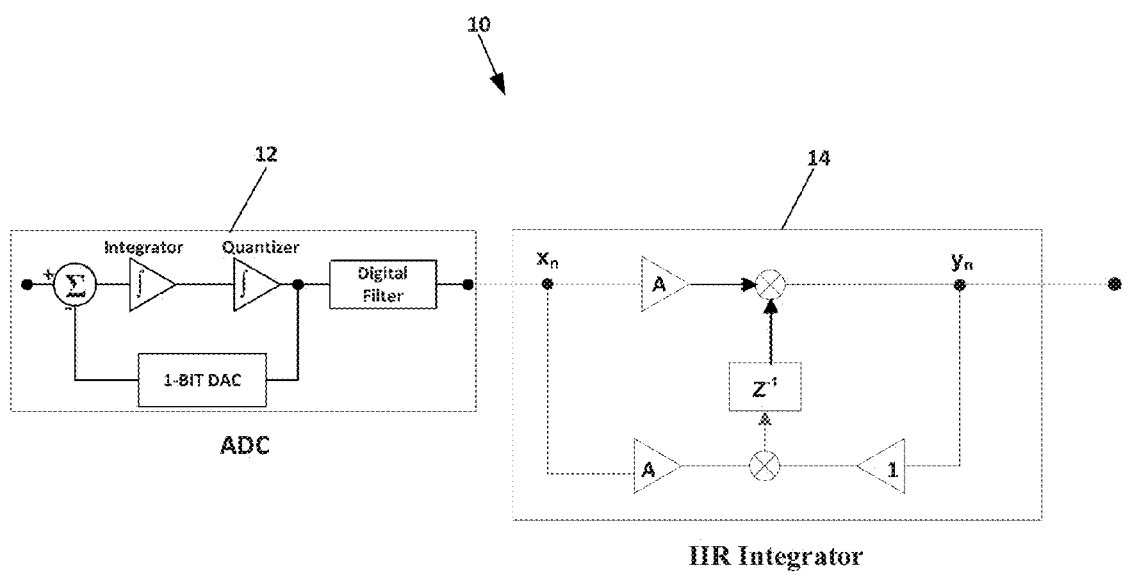
FIG. 1 depicts an ideal real-time integrator according to an embodiment of the invention.

The basic structure for an ideal real-time integrator system 10 is depicted in FIG. 1. The ideal system 10 includes an analog-to-digital converter (ADC) 12 and an ideal integrator 14. The ideal integrator 14 may be implemented using a difference equation which requires only one multiply operation, two addition operations and one storage location per ADC clock cycle. This difference equation is expressed as:

$$y_n := y_{n-1} + A(x_n + x_{n-1}), \quad (1)$$

where $y_n$ is the current output value, $x_n$ is the current input value, $y_{n-1}$ is the previous output value and $x_{n-1}$ is the previous input value. In equation (1), A is a constant derived from the conversion factor.

The difference equation (1) may be derived by taking the ideal integrator transfer function in the s-domain (complex frequency domain) according to:

$$H(s) := \frac{A}{s} \quad (2)$$

where $$s := 2 \cdot \frac{(1-z^{-1})}{dt \cdot (1+z^{-1})}. \quad (3)$$

Applying the bilinear transform results in the following relationship:

$$X(Z) \cdot X(1+Z^{-1}) := \frac{Y(Z) \cdot (1-Z^{-1})}{A} \quad (4)$$

Rearranging terms and applying the inverse Z transform results in the time domain difference equation (1).

The difference equation (1) may be implemented in a digital signal processor (DSP) or general purpose processor as a first order IIR filter. The problems inherent to the ideal integrator as described above are also found in the digital implementation. The infinite gain at DC amplifies low-frequency noise and offsets, and the constant of integration remains in the output sequence. Using the analog implementation as a guide, the digital equivalent of the band-limited integrator can be created using the method described above. The resultant difference equation is given by:

$$y_n = A \cdot x_n + B \cdot x_{n-2} + C \cdot y_{n-1} + D \cdot y_{n-2} \quad (5)$$

where $x_{n-2}$ is the input value prior to $x_{n-1}$, $y_{n-2}$ is the output value prior to $y_{n-1}$, and A, B, C and D are constants determined by the desired high-pass frequency and integrator conversion factor. This filter requires four multiply operations, three addition operations and two storage locations per ADC clock cycle which can be efficiently implemented in most processors.

Figure 2:
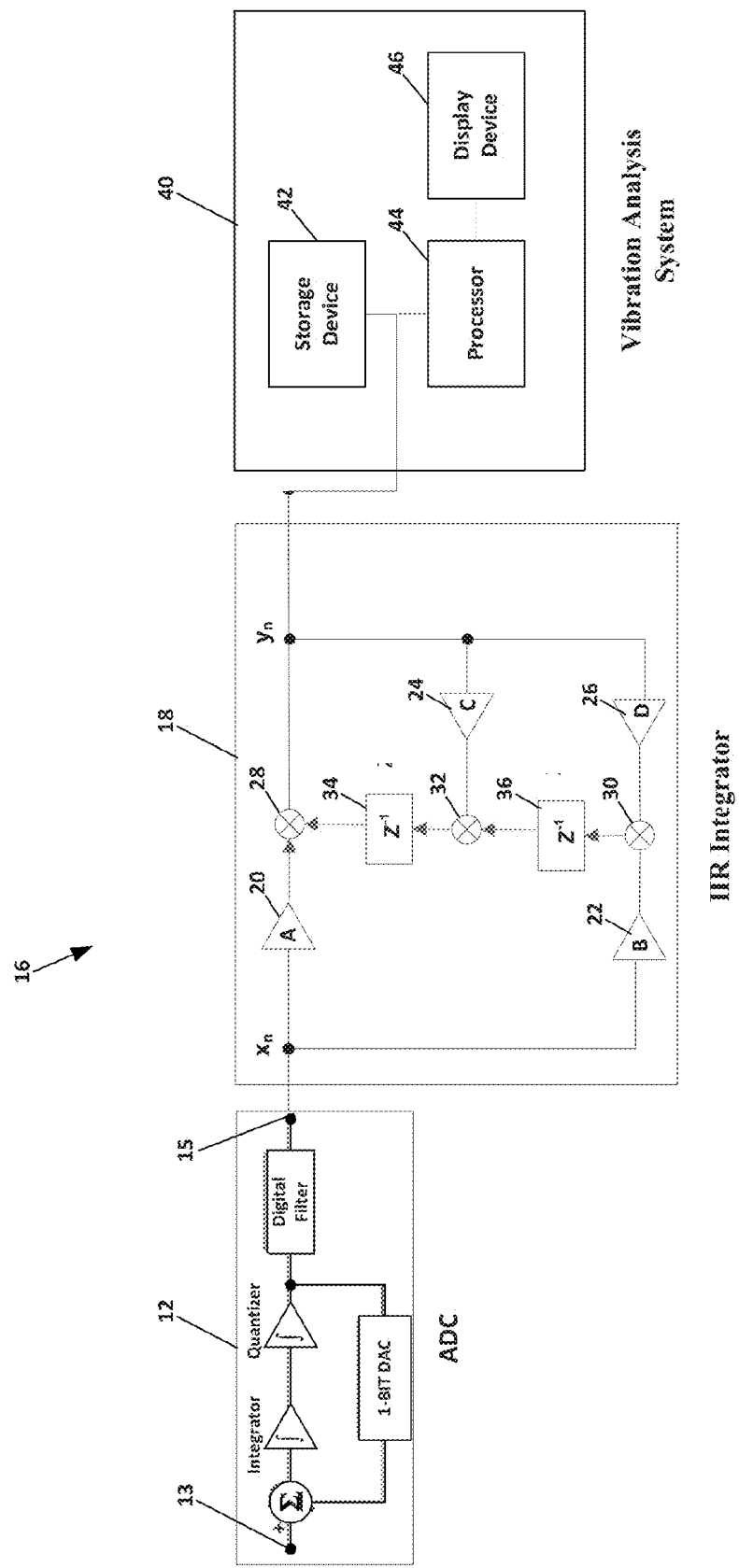
FIG. 2 depicts a band-limited real-time integrator according to an embodiment of the invention.

FIG. 2 depicts an embodiment of a signal conversion apparatus 16 which implements the filter of equation (5). This embodiment of the apparatus 16 includes an ADC 12 and an infinite impulse response (IIR) filter module 18. A time-domain analog vibration-related signal, such as an accelerometer signal measured at some point of interest on a machine, is applied to an input 13 of the ADC. The time-domain analog vibration-related signal could also be a velocity signal or a displacement signal. The ADC 12 converts the analog vibration-related signal into a first time-domain digital signal, $x_n$, at the output 15 of the ADC 12. The signal, $x_n$, is provided to the filter module 18 which generates a second time-domain digital signal, $y_n$, at its output according to the filter of equation (5).

As shown in FIG. 2, a preferred embodiment of the filter module 18 includes a multiply operation 20 for implementing the $A \cdot x_n$ operation, a multiply operation 22 for implementing the $B \cdot x_{n-2}$ operation, a multiply operation 24 for implementing the $C \cdot y_{n-1}$ operation, and a multiply operation 26 for implementing the $D \cdot y_{n-2}$ operation. The filter module 18 also includes three addition operations 28, 30 and 32, and two unit delay storage operators 34 and 36.

The output of the filter module 18 is provided to a vibration analysis system 40 which preferably comprises a computer processor 44, digital storage device 42 and display device 46. The vibration analysis system 40 may be implemented in a handheld vibration analyzer, in a notebook computer, a desk top computer or server. The vibration analysis system 40 receives the second time-domain digital signal, $y_n$, which may be an acceleration signal, velocity signal or displacement signal, and processes the signal, $y_n$, to provide machine vibration data in a format that is useful to a machine vibration analyst. The processed machine vibration data may be displayed on the display device 46 for observation by the vibration analyst or stored on the storage device 42 for subsequent processing or display.

It will be appreciated that the filter module 18 may be implemented in a digital signal processor, general purpose processor, or implemented entirely in hardware as in an FPGA or ASIC that is separate from the processor 44 of the vibration analysis system 40, or the filter module 18 may be implemented in the processor 44.

In alternative embodiments of the invention, the first time-domain digital signal, $x_n$, at the output of the ADC 12 is stored in a digital storage device, such as the device 42, as the data is sampled. The stored signal, $x_n$, may subsequently be processed by the filter module 18 to generate the second time-domain digital signal, $y_n$. In this manner, the system 16 provides the ability to directly integrate or differentiate stored time-domain waveforms without resorting to FFT processing methods.

As will be appreciated by those skilled in the art, the topology for a differentiator implementation of the filter 18 is substantially identical to that depicted in FIG. 2, and only requires different values of the coefficients A, B, C and D.

Figure 3:
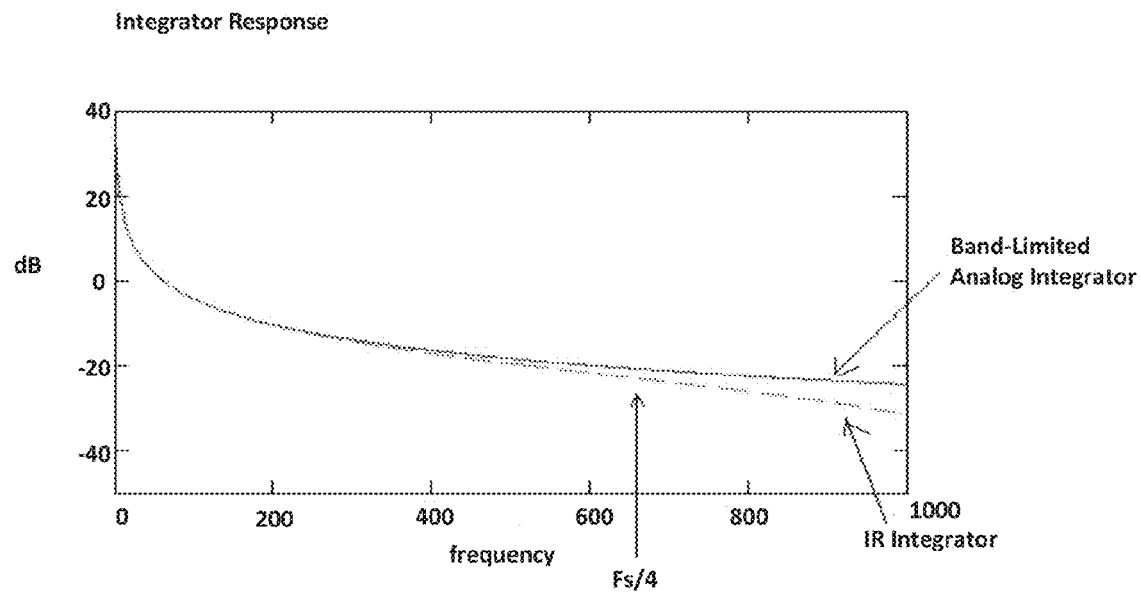
FIG. 3 depicts a frequency response curve for an IIR integrator and a band-limited analog integrator.
Figure 4:
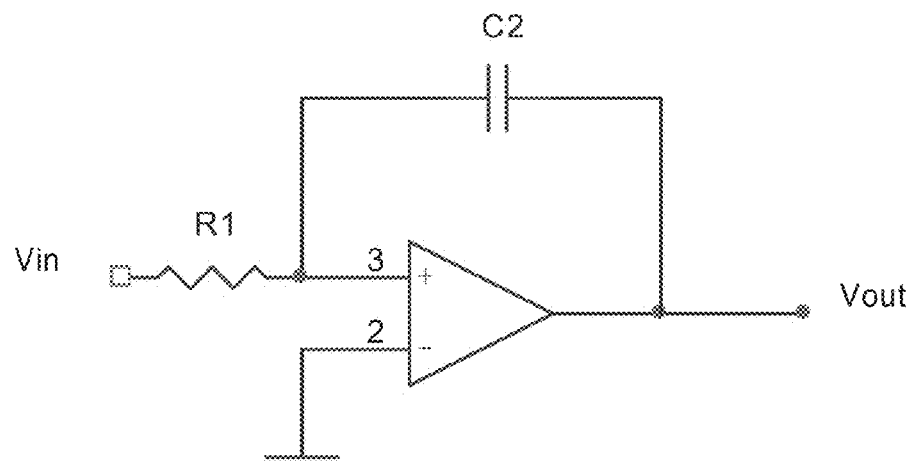
FIG. 4 depicts an ideal hardware integrator.
Figure 5:
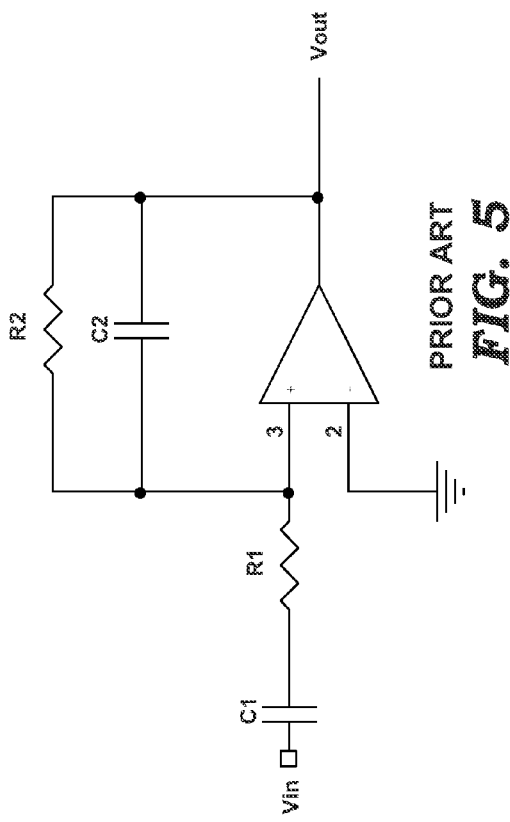
FIG. 5 depicts an band-limited hardware integrator.

For optimum results, the sampling data rate should be at least twice the Nyquist frequency (Fs/2) due the frequency warping of the bilinear transform process. As shown in FIG. 3, the IIR implementation begins to deviate from the ideal case at about Fs/4. In practice, this is not a severe limitation, as over-sampling is often required for other related vibration analysis functions.

In summary, by implementing the integration function in the digital data stream, vibration units are efficiently transformed in real time with very little data storage and with complete flexibility in the conversion type.

Digital Vibration Signal Conditioning

Figure 8:
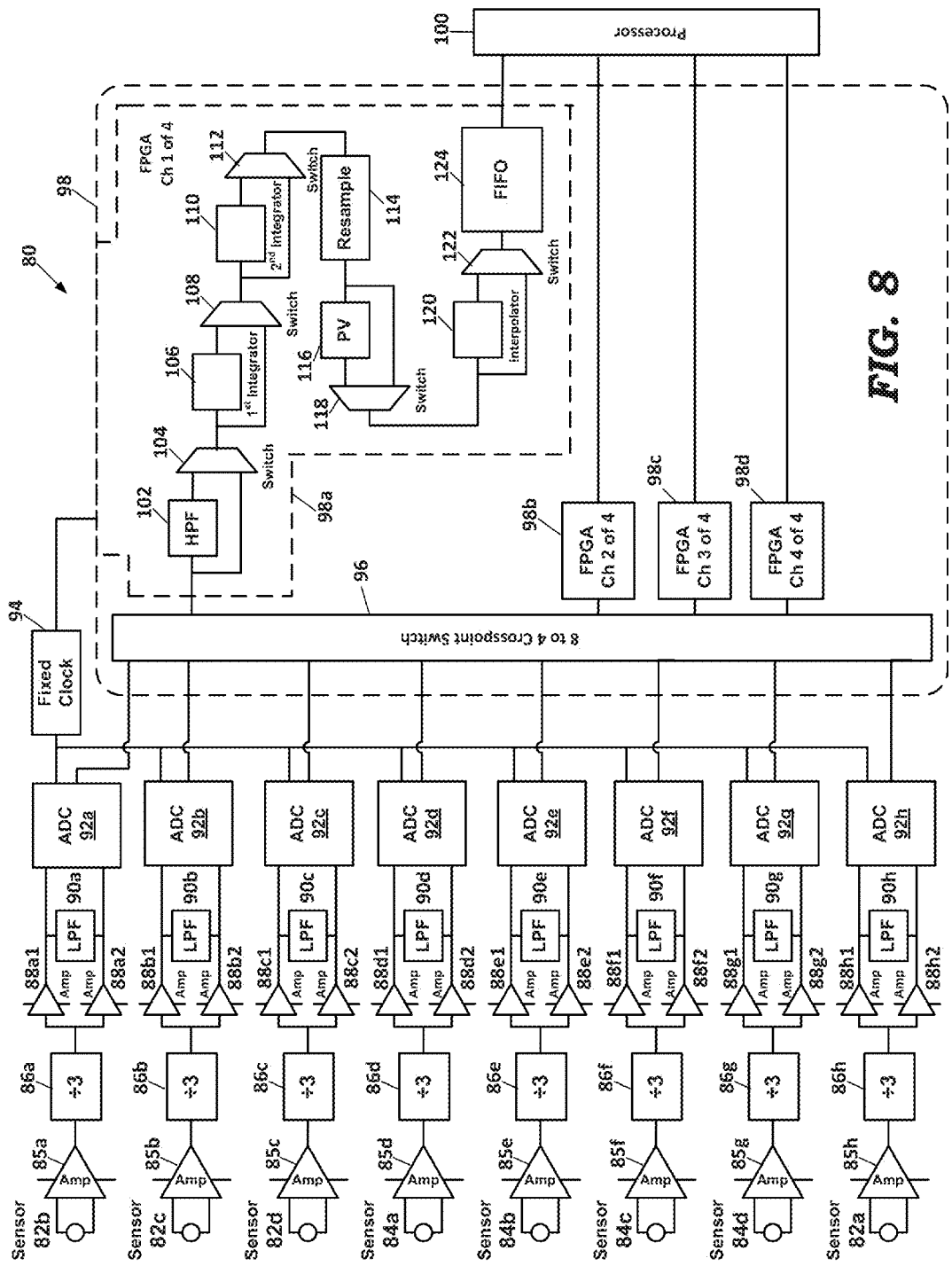
FIG. 8 depicts a multi-channel machine vibration measurement system in which signal conditioning functions are performed digitally in a field programmable gate array.

FIG. 8 depicts a preferred embodiment of a multi-channel machine vibration measurement apparatus 80 that performs signal conditioning functions in the digital domain. In this embodiment, the analog front end includes eight input sensors 82a-82d and 84a-84d. Although the invention is not limited to any particular type of sensor, the sensors 82a-82d are preferably accelerometers and the sensors 84a-84d are preferably voltage sensors. In one embodiment, one or more of the sensors 82a-82d or 84a-84d are cameras for capturing visual images of a machine which is also being monitored for vibration using other of the sensors 82a-82d and 84a-84d. After each of the sensors 82a-82d and 84a-84d, the analog signal chain includes a differential amplifier 85a-85h, a divide-by-3 circuit 86a-86h, differential amplifier pairs 88a1-88h1 and 88a2-88h2, and low pass filters 90a-90h. These eight analog sensor channels are provided to the inputs of eight 24-bit sigma-delta analog-to-digital converters (ADC's) 92a-92h whose sampling rates are dictated by a fixed clock 94.

The high-pass filter 102 removes the DC component of the signal at its input. The switch 104 provides for bypassing the high-pass filter 102 for those applications in which the DC bias of a signal needs to be measured.

The first integrator 106 provides for integrating an acceleration signal to convert it into a velocity signal. In a preferred embodiment, the first integrator 106 is an IIR integrator that is structurally and functionally equivalent to the integrator 18 (in FIG. 2) described above. In alternative embodiments, the first integrator 106 may implement other integrator schemes which use other integration algorithms. The switch 108 provides for bypassing the first integrator 106 for those applications in which the first stage of integration is not desired.

The second integrator 110 provides for integrating a velocity signal to convert it into a position signal. In a preferred embodiment, the second integrator 110 is an IIR integrator that is structurally and functionally equivalent to the first integrator 106. In alternative embodiments, the second integrator 108 may implement other integrator schemes which use other integration algorithms. The switch 112 provides for bypassing the second integrator 110 for those applications in which the second stage of integration is not desired. For example, the second integrator 110 may be bypassed when only the first integrator 106 is needed to convert acceleration to velocity. Both integrators 106 and 110 may be bypassed when the desired output is acceleration. Both integrators 106 and 110 may be used when the desired output is displacement.

In some embodiments, one or both of the integrators 106 and 110 in at least one of the FPGA channels 98a-98d are operable to perform a double integration of the vibration signal at its input. For example, the first integrator 106 may receive an acceleration signal and perform a double integration to provide a displacement signal at its output without producing an intermediate velocity signal during the integration process. In this embodiment, the second integrator 110 may be bypassed using the switch 112 so that the resampler 114 receives the displacement signal from the first integrator 106. In an alternative embodiment, the first integrator 106 may be bypassed using the switch 108 so that the second integrator 110 receives an acceleration signal, and the second integrator 110 performs a double integration to provide a displacement signal at its output. In yet another embodiment, at least one of the FPGA channels 98a-98d includes only a single integrator that receives an acceleration signal and performs a double integration to provide a displacement signal at its output without producing an intermediate velocity signal during the integration process.

The arbitrary resampler 114 extracts some subset of data points from the data stream at its input. For example, the resampler 114 may extract every other data point or every third data point and discard the others. In some embodiments, the resampler 114 performs the functions of a decimator. The resampling factor is arbitrary in that it may be selected by a user to provide the signal frequency components desired by the user for a particular analysis application.

The PeakVue module 116 performs one or more processes for determining peak amplitude vibration values during predetermined sample time periods. These processes, which are referred to and widely known in the industry as "PeakVue," are described in U.S. Pat. No. 5,895,857 to Robinson et al., the entire contents of which are incorporated herein by reference. The switch 118 provides for bypassing the PeakVue module 116 for those applications in which the desired output includes all data points in a sample period, and not just the peak amplitude values.

The interpolator 120 adds new data points between existing data points to recreate waveform details. This effectively increases the "sample rate" of the signal which is advantageous for some analysis applications, such as orbital data analysis. The switch 122 provides for bypassing the interpolator 120 for those applications in which an increase in sample rate is not needed.

The FIFO 124 allows the FPGA 98 to generate vibration data in real time while allowing the processor 100 to access the data asynchronously.

The processor 100 receives the vibration signal data from each of the four FPGA channels 98a-98d and performs one or more vibration analysis functions, such as statistical analysis (RMS, standard deviation, crest factor, etc.), other waveform analysis techniques suggested by Piety et. al. in U.S. Pat. No. 5,943,643, and FFT calculations. The processor 100 also handles user interface and display functions. In alternative embodiments, some or all of the functions performed by the processor 100 may be performed by the FPGA 98.

In a preferred embodiment of the system of FIG. 8, the ADC's 92a-92h are very high quality 24-bit sigma-delta converters. The latest generation of these ADC's have dynamic ranges of greater than 120 dB and signal-to-noise ratios greater than 110 dB. With this much dynamic range, the entire voltage input range can be acquired with sufficiently high resolution to eliminate the need for gain amplifiers and AC coupling amplifiers (such as the amplifiers 62 and 66 of FIG. 7). Because the large dynamic range of the ADC's 92a-92h provides for resolving small AC signals superimposed on large DC offsets, sensor output signals can be directly coupled to the ADC's, and DC components can be removed by real-time digital filtering in the FPGA 98.

Figure 7:
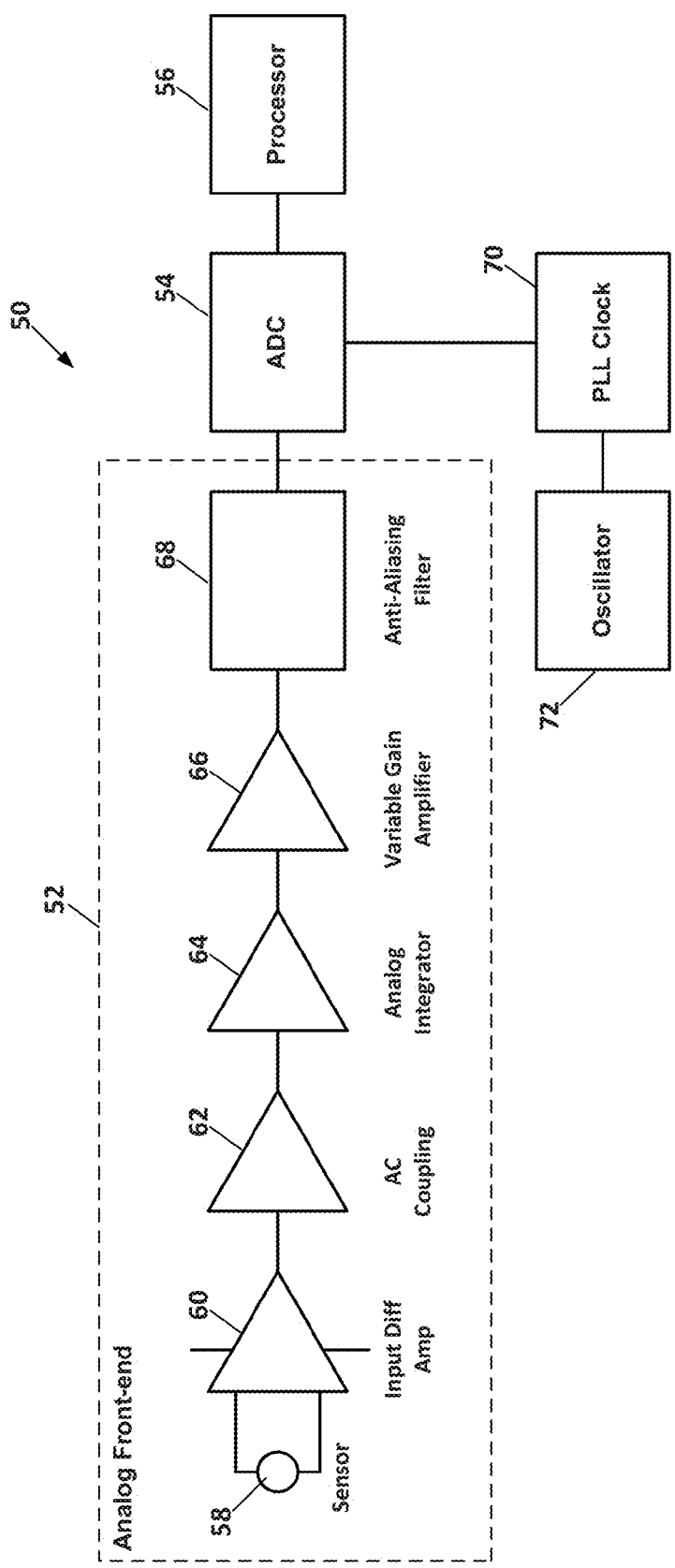
FIG. 7 depicts a conventional machine vibration measurement system in which signal conditioning functions are performed by analog components.

In prior multi-frequency designs, an analog front-end (such as depicted in FIG. 7) must implement some form of filter to ensure no aliasing occurs at low ADC sampling frequencies. Typically, an analog anti-aliasing filter (such as 68 in FIG. 7) must have a sharp cutoff and very little amplitude distortion to preserve the quality characteristics of the ADC. These filters often dictate the overall amplitude and phase accuracy of the system.

In contrast, the ADCs implemented in the embodiments described herein have little or no anti-aliasing filter requirements at a fixed frequency. Preferred embodiments of the present invention avoid the aliasing problems of prior analog designs by running the ADC's 92a-92h at a fixed clock frequency and synthesizing all other samples rates by decimation and interpolation of the digital ADC data stream. The anti-aliasing filter can then be replaced by a simple RC circuit at the input of the ADC (such as the low pass filters 90a-90h shown in FIG. 8) or, in some embodiments, eliminated altogether.

A further advantage of the embodiment of FIG. 8 is the reduction of the data rate seen by the processor 100. This is particularly advantageous in multi-channel systems like the embodiment of FIG. 8 where the processor 100 handles multiple data streams. For high-speed processes like the PeakVue application, offloading the bulk of the high-pass filtering and decimation to an FPGA reduces the interrupt rate to the processor by a factor of 20.

Because preferred embodiments of the device 80 are field programmable, an operator can completely reconfigure the device in the field to switch between (a) slow-speed technology (SST) processing (such as described in U.S. Pat. No. 5,646,350 to Robinson et al.) which prevents high frequency components of an accelerometer signal from overwhelming low freqeuncy components as a result of dynamic range loss during processing of the accelerometer output, (b) PeakVue processing wherein a peak scalar value is determined for each measurment time interval, (c) triaxial sensor processing wherein signals from three accelerometers mounted in orthogonal orientations in a single sensor package are simultaneously processed and wherein one such signal is simultaneously processed multiple ways for multiple purposes, and (d) normal vibration analysis wherein a sensor signal is processed in a frequency range of interest to detect and analyze possible machine fault conditions. For example, the FPGA may be reconfigured by the host processor 100 (or on-board processor 132 of FIG. 9) using firmware configuration files stored in the device 80, or using files that are downloaded to the device 80 via a wireless link, a USB interface, or a nonvolatile memory card (such as an SD card).

Preferred embodiments are also scalable. Although the exemplary device 80 depicted in FIG. 8 provides eight measurement channels and four FPGA channels, it will be appreciated that practically any number of measurement channels and FPGA channels are possible with the appropriate cross-point switch. This is particularly advantageous for online vibration monitoring and machine shutdown protection systems. In vibration measurement systems, scalability means to the ability to increase the number of processing channels (such as the channels 98a-98d) in an efficient manner. In general, the cost per channel of an FPGA implementation (in dollars, power consumption, and size) goes down as the number of channels in the FPGA increases.

By elimination of sequential processing and discrete components, preferred embodiments such as shown in FIG. 8 significantly increase the speed of vibration data processing as compared to sequential systems such as shown in FIG. 7. This speed increase results in a vibration measurement system that is fast enough to comply with machine shutdown protection standards such as those specified in American Petroleum Institute (API) standard 670.

Also, through filtering and arbitrary resampling decimation, large amounts of unneeded data are eliminated in the FPGA 98 of the preferred embodiment. This frees memory and computational resources in the processor 100 that would otherwise be tied up with data reduction tasks.

For transient data processing, each FPGA channel 98a-98d can perform a processing task that is completely independent of processing tasks being performed simultaneously in the other channels. This includes the ability to select different processing bandwidths for each channel.

The preferred embodiment depicted in FIG. 8 is ideally suited for integration of imaging analysis and dynamic signal analysis as described in U.S. Pat. No. 7,561,200 to Garvey et al (the '200 patent), incorporated entirely herein by reference. Embodiments of the present invention are purposely suited for simultaneous parallel processing. In one such parallel circuit path, images are received and stored, and indications of equipment health are derived from such imagery. Example images include (a) thermal imagery revealing temperature indications, (b) bore sighted imagery revealing machine component operation and component defect information, (c) visible inspection imagery revealing physical condition and movement and proximity of subassemblies, and (d) variable speed imagery revealing strobe-synchronous operation. Simultaneously on a parallel circuit path, an instrument according to a preferred embodiment receives dynamic sensor data and further derives a dynamic indication of equipment health. Example dynamic sensor data include (a) vibration sensor output, (b) motor current information measured directly or indirectly using a current clamp, (c) motor flux information measured using a flux coil, and (d) ultrasonic sensor output. FPGA and ASIC circuits of the present invention are well suited to simultaneously process these parallel processes, permitting correlation between an imagery indication of equipment health and a simultaneous dynamic signal indication of equipment health. Exemplary imagery indications of equipment health and dynamic signal indications of equipment health are described in the '200 patent in column 6, line 1 to column 7, line 18. A correlation between imagery and dynamic indications of equipment health, or lack of such correlation, is valuable to the analyst because they provide totally independent views of machine health. When both or neither give similar problematic indication, likelihood of correctness is high, often justifying prompt action possibly without further verification. When they produced dissimilar problematic indications, then an operator is inclined to look for further verification before taking action with expensive consequence.

As discussed above, each of the processing functions associated with the FPGA embodiment of FIG. 8 may also be implemented in an Application Specific Integrated Circuit (ASIC) embodiment. An ASIC embodiment provides for implementation of smart sensor concepts as described in U.S. Pat. No. 6,138,078 to Canada et al. (the '078 patent), and in U.S. Pat. No. 5,854,994 to Canada et al. (the '994 patent), where small circuit board footprint, high speed processing, low power consumption, and low cost are critical factors.

Whether implemented in FPGA or ASIC configuration, embodiments of the present invention reduce circuit size and rate of power consumption, thereby reducing package size and installed cost. All of these factors are critical enabling aspects for widespread acceptance and deployment of a monitor with tethered sensors as described in the '078 patent, or of stand-alone wireless monitors as described in the '994 patent. Low power consumption is crucial for these remote monitors, whether they are battery powered or their power is supplemented using an energy harvesting technique such as vibration energy harvesting, examples of which are PGM-series power solutions from Perpetuum and Joule-Thief™ Capacitive EHD Modules available from AdaptiveEnergy. In energy harvesting applications, calculations performed in an FGPA or ASIC could be made to determine at which frequencies the peak vibration energy is located. Based on this determination, electrical characteristics of the energy harvesting system may be automatically adjusted to cause the energy harvesting system to access the vibration energy from those peak frequencies.

Figure 6:
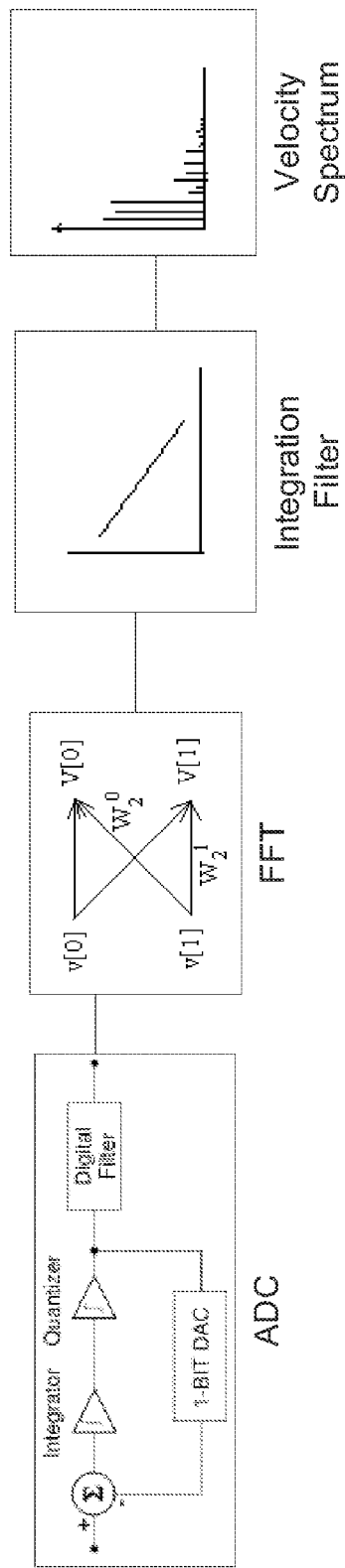
FIG. 6 depicts an FFT vibration data processing system.

Smaller package size improves usefulness and sometimes even viability for stand-alone monitors mounted wherein meaningful mechanical vibrations over a range of frequencies must be sensed through a physical connection between each monitor housing and a machine surface, such as the attachment means described in the '994 patent which is depicted as 404 on FIG. 2 of the '994 patent. The present invention delivers significant advantage for a wireless machine mounted vibration monitor regarding power consumption, package size and unit cost; wherein the size, component count, and supporting resource requirements for circuit shown in FIG. 6 of the '994 patent are substantially reduced and by removing the analog AMP 412 and analog FILTER 414 and performing these processes in the digital domain using an FPGA or ASIC based circuit of the present invention in place of the DATA PROCESSOR 420 of the COMPUTER 418 shown in FIG. 6 of the '994 patent.

In addition to the stationary plurality of machine monitors as depicted by Canada et al in FIG. 1 of '994, the present invention can be used in form of a route-based walk-around sensor wherein a wireless communication technique, for example Bluetooth or other radio frequency communication, is used to transmit digital data from the sensor, thereby replacing traditional cabled analog signal communication. Instead of installing nine stationary monitors like 4a to 4i from FIG. 1 of '994, in the walk-around sensor user may use a single sensor to collect data from these nine locations and others if called for. There are at least two options for receiving vibration data from such a walk-around sensor: the vibration data may be received by an operator carried (in hand, on wrist, on clothing, or with gear) wireless transceiver, or it may be transmitted along paths like what is outlined in FIG. 1 of '994.

With the available speed and flexible processing options provided by preferred embodiments of the invention, PeakVue and SST processing may be enhanced. By replacing external analog hardware with its digital equivalent in an FPGA, it is possible to change the signal processing parameters adaptively. For example, though it is difficult to change corner frequencies on an analog integrator, this is a trivial change for an integrator implemented as a filter in an FPGA. PeakVue, which is a scalar peak value determination methodology often used to characterize stress waves produced by impacting, can be enhanced using embodiments of the invention by determining information in addition to the scalar value, such as peak-rise characteristic, peak-fall characteristic, other peak shape aspects, and information regarding peaks nearby to the maximum peak. Acquisition of such information is not practical using prior art peak detection techniques.

Yet another advantage of eliminating analog signal conditioning circuitry is the elimination of any need to do drift or calibration compensation which is normally required with this analog circuitry.

Further advantages of FPGA technology in vibration monitoring systems include the following.

- Its parallel nature provides for performing many types of data analysis simultaneously in parallel paths. This aspect of the present invention is advanced beyond the systems described by Piety et al in U.S. Pat. No. 5,965,819 wherein multiple ADCs and multiple processors are used to simultaneously process multiple signals from one sensor. It is also advanced beyond the systems described by Leigh in U.S. Patent Application 2006/0150738 wherein a processor sequentially, not simultaneously, processes multiple signals from a single sensor.
- As semiconductor technology evolves, FPGA technology insulates hardware designs from obsolete component issues.
- Using FPGAs, signal processing can be tailored for a particular application with a high degree of precision. For example, it is possible to arbitrarily define the bit width of the data processing in an FPGA to match resolution requirements of a particular measurement. Using conventional technology, bit width choices are limited to predefined values, such as 8-bit, 16-bit, and 24-bit.

Figure 9:
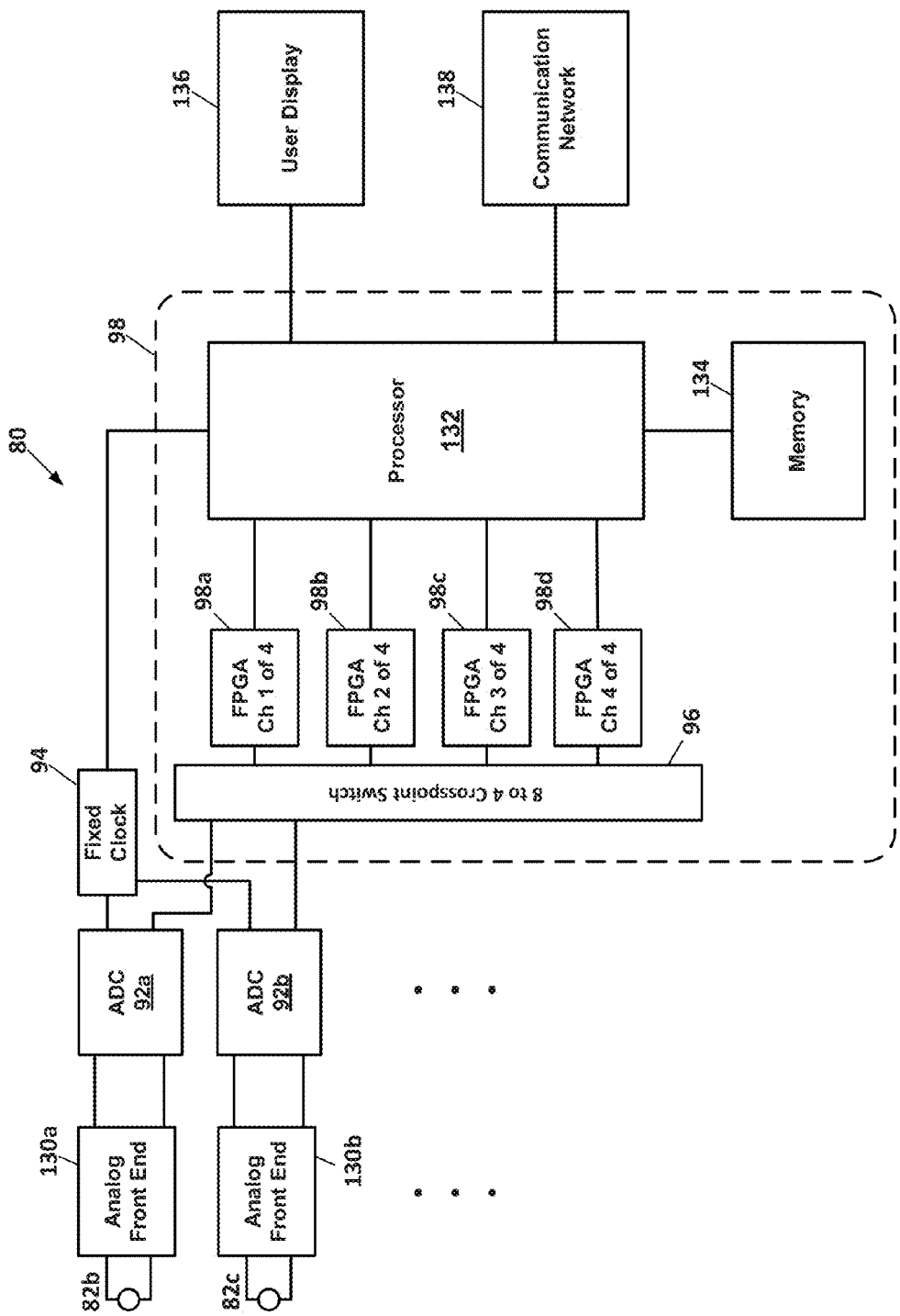
FIG. 9 depicts a multi-channel machine vibration measurement system in which signal conditioning functions are performed digitally in a field programmable gate array that includes an embedded processor.

FIG. 9 depicts another embodiment of a multi-channel machine vibration measurement apparatus 80 that performs signal conditioning functions in the digital domain. This embodiment is substantially the same as the embodiment of FIG. 8 except that the FPGA 98 includes an embedded processor 132 for controlling the storage and processing of the vibration data from the FPGA channels 98a-98d. The analog components 85a, 85b, 86a, 86b, 88a1, 88a2, 88b1, 88b2, 90a, and 90b depicted in FIG. 8 are represented in FIG. 9 by the "analog front end" blocks 130a and 130b. Although the other sensor analog channels and ADC's of FIG. 8 are included in the embodiment of FIG. 9, they are not depicted in FIG. 9 to simplify the drawing.

In a preferred embodiment, the embedded processor 132 of FIG. 9 also controls a user display device 136 and controls communications with an external communication network 138, such as an Ethernet, serial, or HART network.

Figure 10:
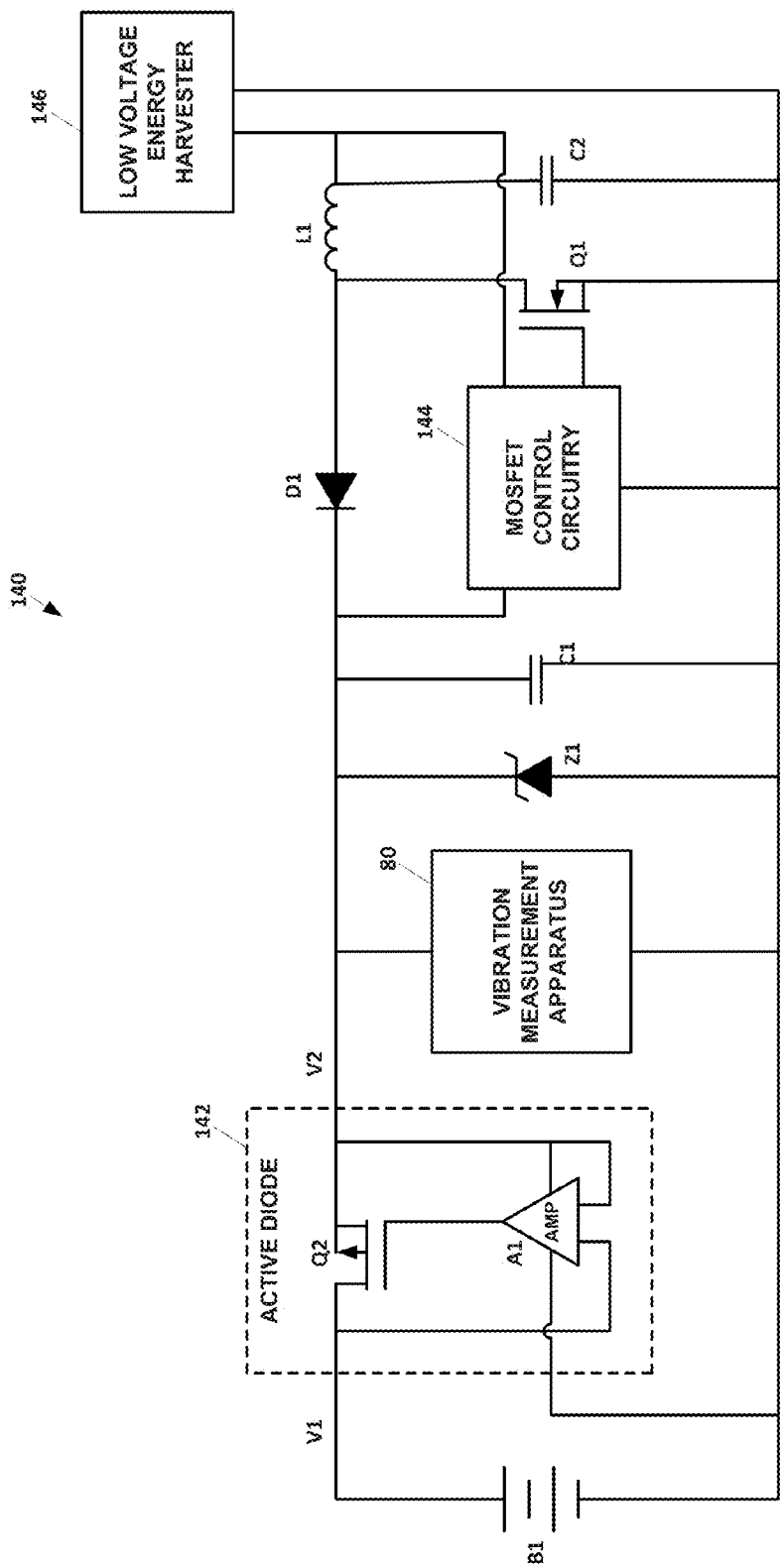
FIG. 10 depicts a circuit for providing power to a machine vibration measurement system.

FIG. 10 depicts a preferred embodiment of a circuit for providing power to a vibration measurement apparatus, such as the apparatus 80 shown in FIGS. 8 and 9. This circuit is particularly beneficial when the apparatus 80 is implemented as a wireless vibration measurement apparatus. The circuit implements a hybrid combination of an energy harvester 146 and a non-rechargeable battery B1 which does not use traditional energy storage in advance of a DC/DC conversion step. In general, the circuit supplements the power of the primary battery cell (or cells) B1 with power from the energy harvestor 146.

As shown in the embodiment of FIG. 10, the positive terminal of the non-rechargeable battery B1 drives the anode side of a discrete diode, or of an active diode circuit 142, as is shown in simplified form. When the voltage V1 on the anode side is greater than the voltage V2 on the cathode side, current flow can occur through the active diode 142. When the voltage V2 is greater than the voltage V1, current flow through the diode 142 is prohibited. Power from the energy harvestor 146 feeds a simple voltage booster consisting of inductor L1, diode D1, silicon switch Q1, and switch control circuitry 144. Although a metal-oxide-semiconductor field-effect transistor (MOSFET) switch Q1 is used in this embodiment, other device types, such as a bipolar transistor, could alternatively be employed. The availability of primary cell power simplifies the design of the switch control circuitry 144, as no bootstrapping is required, even for cases of very low voltage scavenged energy from the energy harvestor 146. The switch control circuitry 144 can optionally be disabled when scavenged energy is not available, thereby conserving power. Capacitors C1 and C2 provide filtering for the switching activity. Zener diode Z1 sets the maximum of the voltage V2 to some value higher than the voltage V1 of the primary cell B1. When the energy requirement of the vibration measurement apparatus 80 is less than the power available from the energy harvestor 146, the voltage V2 rises above the voltage V1, and no power is drawn from the primary cell B1. When the power requirement of the vibration measurement apparatus 80 is greater than the power available from the energy harvestor 146, the voltage V2 falls below the voltage V1, and the additional needed power is drawn from the cell B1.

In the presence of the hysteresis, and based on comparator tolerances, reverse diode flow through the active diode 142 may be possible. In some embodiments, the active diode 142 includes a small amount of positive feedback for hysteresis and possibly a small added offset voltage for preventing such reverse diode flow.

The energy harvester 146 may consist of piezoelectric crystals or fibers that generate a small voltage when they are mechanically deformed, such as due to vibration from a machine on which the energy harvester 146 is mounted. The energy harvester 146 may also be a solar panel, or a thermoelectric generator (TEG) formed by the junction of two dissimilar materials in the presence of a thermal gradient. Typically, such energy harvesters produce low power which must be accummulated in an energy storage device such as a super capacitor or a rechargeable battery or another component. The circuit of FIG. 10 eliminates this energy storage step. If the live energy from the energy harvester 146 is sufficient to carry the load, then it is used. If the live energy from the energy harvester 146 is not sufficient to entirely carry the load, then a switch is performed and the battery B1 supplies the entire load until the load requirement can again be met by the energy harvester 146.

Preferably, the battery B1 is a non-rechargeable battery, such as a Tidran Lithium battery which provides very reliable and long-shelf-life energy in an industrial environment. The size of the battery B1 is preferably determined based on the maximum power spikes needed intermittently. An exemplary wireless vibration monitoring device, such as the CSI 9420 from Emerson Process Management, is likely to be in low-power or sleep mode for more than 99.9% of life and will require battery power for less than 0.1% of life.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A real-time signal conversion apparatus for use in measuring machine characteristics that are indicative of a machine fault condition or machine performance, the signal conversion apparatus comprising:
    a first sensor for sensing a machine characteristic at a first position and generating a first analog signal;
    a second sensor for sensing a machine characteristic at a second position and generating a second analog signal;
    analog-to-digital conversion (ADC) circuits comprising at least:
        a first ADC circuit for sampling the first analog signal to generate a first digital signal; and
        a second ADC circuit for sampling the second analog signal to generate a second digital signal,
        wherein the first and second digital signals are indicative of machine performance or a machine fault condition;
    an integrated circuit component having at least two parallel channels for simultaneously processing the first digital signal in parallel with the second digital signal, the first digital signal in parallel with the first digital signal, or the second digital signal in parallel with the second digital signal, the at least two parallel channels including:
        a first channel for processing the first digital signal or the second digital signal; and
        a second channel for processing the first digital signal or the second digital signal; and
    a cross-point switching device that is operable to provide the first digital signal to the first or second channels, and to provide the second digital signal to the first or second channels;
    wherein the first and second channels each include:
        a first integrator for integrating the first or second digital signals;
        a first integrator bypass switch for selectively bypassing the first integrator for applications in which a first stage of integration is not needed;
        a second integrator in series with the first integrator, the second integrator for integrating the first or second digital signals; and
        a second integrator bypass switch for selectively bypassing the second integrator for applications in which a second stage of integration is not needed.

2. The real-time signal conversion apparatus of claim 1 wherein the first digital signal is a first acceleration signal and the second digital signal is a second acceleration signal, and wherein:
    the cross-point switching device is operated in the first setting to direct the first acceleration signal to the first channel and to the second channel;
    the first integrator bypass switch of the first channel is set to not bypass the first integrator of the first channel, and the second integrator bypass switch of the first channel is set to not bypass the second integrator of the first channel;
    the first integrator of the first channel performs a single integration of the first acceleration signal to generate a first velocity signal, and the second integrator of the first channel performs a single integration of the first velocity signal to generate a first displacement signal, resulting in the first displacement signal being output from the first channel;
    the first integrator bypass switch of the second channel is set to not bypass the first integrator of the second channel, and the second integrator bypass switch of the second channel is set to bypass the second integrator of the second channel; and
    the first integrator of the second channel performs a single integration of the first acceleration signal to generate a first velocity signal, resulting in the first velocity signal being output from the second channel.

3. The real-time signal conversion apparatus of claim 1 wherein the first digital signal is a first acceleration signal and the second digital signal is a second acceleration signal, and wherein:
    the cross-point switching device is operated in the first setting to direct the first acceleration signal to the first channel and to the second channel;
    the first integrator bypass switch of the first channel is set to bypass the first integrator of the first channel, and the second integrator bypass switch of the first channel is set to bypass the second integrator of the first channel, resulting in the first acceleration signal being output from the first channel;
    the first integrator bypass switch of the second channel is set to not bypass the first integrator of the second channel, and the second integrator bypass switch of the second channel is set to bypass the second integrator of the second channel; and
    the first integrator of the second channel performs a single integration of the first acceleration signal to generate a first velocity signal, resulting in the first velocity signal being output from the second channel.

4. The real-time signal conversion apparatus of claim 1 wherein the first digital signal is a first acceleration signal and the second digital signal is a second acceleration signal, and wherein:
    the cross-point switching device is operated in the first setting to direct the first acceleration signal to the first channel and to the second channel;
    the first integrator bypass switch of the first channel is set to not bypass the first integrator of the first channel, and the second integrator bypass switch of the first channel is set to bypass the second integrator of the first channel;

the first integrator of the first channel performs a double integration of the first acceleration signal to generate a first displacement signal, resulting in the first displacement signal being output from the first channel;

the first integrator bypass switch of the second channel is set to not bypass the first integrator of the second channel, and the second integrator bypass switch of the second channel is set to bypass the second integrator of the second channel; and the first integrator of the second channel performs a single integration of the first acceleration signal to generate a first velocity signal, resulting in the first velocity signal being output from the second channel.

5. The real-time signal conversion apparatus of claim 1 wherein one or both of the first and second integrators comprise a digital infinite impulse response filter running at an input sampling rate of the one or more ADC circuits, thereby reducing data storage requirements.

\* \* \* \* \*